(12) United States Patent
Dryga et al.

(10) Patent No.: US 9,869,671 B2
(45) Date of Patent: *Jan. 16, 2018

(54) ANALYZING BACTERIA WITHOUT CULTURING

(71) Applicant: DNAE Group Holdings Limited, London (GB)

(72) Inventors: Sergey A. Dryga, Albuquerque, NM (US); Lisa-Jo Ann Clarizia, Albuquerque, NM (US); Eddie W. Adams, Albuquerque, NM (US); Victor C. Esch, Albuquerque, NM (US)

(73) Assignee: DNAE Group Holdings Limited, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 15/496,790

(22) Filed: Apr. 25, 2017

(65) Prior Publication Data

US 2017/0227535 A1    Aug. 10, 2017

Related U.S. Application Data

(63) Continuation of application No. 13/091,548, filed on Apr. 21, 2011, now Pat. No. 9,671,395.

(60) Provisional application No. 61/326,588, filed on Apr. 21, 2010.

(51) Int. Cl.
| | |
|---|---|
| *C12Q 1/70* | (2006.01) |
| *G01N 33/543* | (2006.01) |
| *C12Q 1/68* | (2006.01) |
| *G01N 33/569* | (2006.01) |
| *B01L 3/00* | (2006.01) |
| *C07K 1/22* | (2006.01) |

(52) U.S. Cl.
CPC .. *G01N 33/54333* (2013.01); *B01L 3/502761* (2013.01); *C12Q 1/689* (2013.01); *G01N 33/56911* (2013.01); *B01L 2200/0647* (2013.01); *B01L 2400/043* (2013.01); *G01N 2333/195* (2013.01)

(58) Field of Classification Search
CPC .... D02G 3/00; D01D 5/00; D01F 1/10; D01F 6/14; D01F 6/16; D01F 8/00; C12M 1/34
USPC ............ 435/29, 30, 173.4, 173.9, 243, 261, 435/287.3, 302.1; 436/174, 177, 526, 538
See application file for complete search history.

(56) References Cited

U.S. PATENT DOCUMENTS

| | | | |
|---|---|---|---|
| 3,970,518 A | 7/1976 | Giaever | |
| 4,018,886 A | 4/1977 | Giaever | |
| 4,180,563 A | 12/1979 | Fauve | |
| 4,230,685 A | 10/1980 | Senyei et al. | |
| 4,267,234 A | 5/1981 | Rembaum | |
| 4,434,237 A | 2/1984 | Dinarello | |
| 4,452,773 A | 6/1984 | Molday | |
| 4,551,435 A | 11/1985 | Liberti et al. | |
| 4,554,088 A | 11/1985 | Whitehead et al. | |
| 4,659,678 A | 4/1987 | Forrest et al. | |
| 4,677,055 A | 6/1987 | Dodin et al. | |
| 4,683,195 A | 7/1987 | Mullis et al. | |
| 4,683,202 A | 7/1987 | Mullis | |
| 4,695,393 A | 9/1987 | Chagnon et al. | |
| 4,795,698 A | 1/1989 | Owen et al. | |
| 4,901,018 A | 2/1990 | Lew | |
| 4,925,788 A | 5/1990 | Liberti | |
| 4,942,124 A | 7/1990 | Church | |
| 4,988,617 A | 1/1991 | Landegren et al. | |
| 5,047,321 A | 9/1991 | Loken et al. | |
| 5,057,413 A | 10/1991 | Terstappen et al. | |
| 5,089,386 A | 2/1992 | Stackebrandt et al. | |
| 5,108,933 A | 4/1992 | Liberti et al. | |
| 5,136,095 A | 8/1992 | Tarnowski et al. | |
| 5,149,625 A | 9/1992 | Church et al. | |
| 5,164,297 A | 11/1992 | Josephson et al. | |
| 5,186,827 A | 2/1993 | Liberti et al. | |
| 5,200,084 A | 4/1993 | Liberti et al. | |
| 5,229,724 A | 7/1993 | Leiger | |
| 5,234,816 A | 8/1993 | Terstappen | |
| 5,242,794 A | 9/1993 | Whiteley et al. | |
| 5,254,460 A | 10/1993 | Josephson et al. | |
| 5,338,687 A | 8/1994 | Lee et al. | |
| 5,342,790 A | 8/1994 | Levine et al. | |
| 5,460,979 A | 10/1995 | Levine et al. | |
| 5,466,574 A | 11/1995 | Liberti et al. | |

(Continued)

FOREIGN PATENT DOCUMENTS

| | | |
|---|---|---|
| CA | 2 342 047 A1 | 9/2001 |
| EP | 1 304 581 A2 | 4/2003 |

(Continued)

OTHER PUBLICATIONS

Sista et al., ( Lab. Chip. 2008. vol. 8(12): 2188-2196).*
Zhao, et al., A rapid bioassay for single bacterial cell quantitation using bioconjugated nanoparticles, PNAS, 101 (42):15027-15032 (2004).
Zordan, et al., Detection of Pathogenic E. coli O157:H7 by a Hybrid Microfluidic SPR and Molecular Imaging Cytometry Device, Cytometry A, 75A:155-162 (2009).
Gu et al., 2003, Using Biofunctional Magentic Nanoparticles to Capture Vancomycin-Resistant Enterococci and Other Gram-Positive Bacteria at Ultralow Concentration, J. Am. Chem. Soc., 125:15702-15703.
Gu et al., 2006, Biofunctional magnetic nanoparticles for protein separation and pathogen detection, Chem. Commun.:941-949.

(Continued)

*Primary Examiner* — Jana A Hines
(74) *Attorney, Agent, or Firm* — Brown Rudnick LLP; Thomas C. Meyers

(57) ABSTRACT

The invention generally relates to conducting an assay on a sample that isolates a pathogen from the sample and allows for analysis of the pathogen with minimal (i.e., at most 24 hrs of culturing) or no culturing of the pathogen. In certain embodiments, the invention provides methods for identifying a pathogen from a sample that involve obtaining a sample including a pathogen, conducting an assay that isolates the pathogen from the sample, culturing the isolated pathogen for at most about 24 hrs, and analyzing the pathogen.

17 Claims, No Drawings

(56) References Cited

U.S. PATENT DOCUMENTS

| | | |
|---|---|---|
| 5,494,810 A | 2/1996 | Barany et al. |
| 5,512,332 A | 4/1996 | Liberti et al. |
| 5,541,072 A | 7/1996 | Wang et al. |
| 5,583,024 A | 12/1996 | McElroy et al. |
| 5,583,033 A | 12/1996 | Terstappen et al. |
| 5,597,531 A | 1/1997 | Liberti et al. |
| 5,604,097 A | 2/1997 | Brenner |
| 5,605,805 A | 2/1997 | Verwer et al. |
| 5,622,831 A | 4/1997 | Liberti et al. |
| 5,622,853 A | 4/1997 | Terstappen et al. |
| 5,636,400 A | 6/1997 | Young |
| 5,646,001 A | 7/1997 | Terstappen et al. |
| 5,654,636 A | 8/1997 | Sweedler et al. |
| 5,660,990 A | 8/1997 | Rao et al. |
| 5,674,713 A | 10/1997 | McElroy et al. |
| 5,677,133 A | 10/1997 | Dberhardt |
| 5,681,478 A | 10/1997 | Lea et al. |
| 5,684,401 A | 11/1997 | Peck et al. |
| 5,695,934 A | 12/1997 | Brenner |
| 5,695,946 A | 12/1997 | Benjamin et al. |
| 5,698,271 A | 12/1997 | Liberti et al. |
| 5,700,673 A | 12/1997 | McElroy et al. |
| 5,741,714 A | 4/1998 | Liberti |
| 5,768,089 A | 6/1998 | Finnigan |
| 5,770,461 A | 6/1998 | Sakazume et al. |
| 5,773,307 A | 6/1998 | Colin et al. |
| 5,776,710 A | 7/1998 | Levine et al. |
| 5,795,470 A | 8/1998 | Wang et al. |
| 5,821,066 A | 10/1998 | Pyle et al. |
| 5,834,217 A | 11/1998 | Levine et al. |
| 5,840,580 A | 11/1998 | Terstappen et al. |
| 5,846,719 A | 12/1998 | Brenner et al. |
| 5,863,722 A | 1/1999 | Brenner |
| 5,866,099 A | 2/1999 | Owen et al. |
| 5,869,252 A | 2/1999 | Bouma et al. |
| 5,876,593 A | 3/1999 | Liberti et al. |
| 5,925,573 A | 7/1999 | Colin et al. |
| 5,935,825 A | 8/1999 | Nishimura et al. |
| 5,948,412 A | 9/1999 | Murphy |
| 5,955,583 A | 9/1999 | Beavo et al. |
| 5,985,153 A | 11/1999 | Dolan et al. |
| 5,993,665 A | 11/1999 | Terstappen et al. |
| 6,013,188 A | 1/2000 | Terstappen et al. |
| 6,013,532 A | 1/2000 | Liberti et al. |
| 6,060,882 A | 5/2000 | Doty |
| 6,097,188 A | 8/2000 | Sweedler et al. |
| 6,100,099 A | 8/2000 | Gordon et al. |
| 6,120,856 A | 9/2000 | Liberti et al. |
| 6,136,182 A | 10/2000 | Dolan et al. |
| 6,138,077 A | 10/2000 | Brenner |
| 6,146,838 A | 11/2000 | Williams et al. |
| 6,150,516 A | 11/2000 | Brenner et al. |
| 6,172,214 B1 | 1/2001 | Brenner |
| 6,172,218 B1 | 1/2001 | Brenner |
| 6,194,900 B1 | 2/2001 | Freeman et al. |
| 6,228,624 B1 | 5/2001 | Terstappen |
| 6,235,475 B1 | 5/2001 | Brenner et al. |
| 6,236,205 B1 | 5/2001 | Ludeke et al. |
| 6,242,915 B1 | 6/2001 | Hurd |
| 6,265,150 B1 | 7/2001 | Terstappen et al. |
| 6,287,791 B1 | 9/2001 | Terstappen et al. |
| 6,307,372 B1 | 10/2001 | Sugarman et al. |
| 6,326,787 B1 | 12/2001 | Cowgill |
| 6,348,318 B1 | 2/2002 | Valkirs |
| 6,352,828 B1 | 3/2002 | Brenner |
| 6,361,749 B1 | 3/2002 | Terstappen et al. |
| 6,361,944 B1 | 3/2002 | Mirkin et al. |
| 6,365,362 B1 | 4/2002 | Terstappen et al. |
| 6,397,094 B1 | 5/2002 | Ludeke et al. |
| 6,404,193 B1 | 6/2002 | Dourdeville |
| 6,456,072 B1 | 9/2002 | Webb et al. |
| 6,469,636 B1 | 10/2002 | Baird et al. |
| 6,487,437 B1 | 11/2002 | Viswanathan et al. |
| 6,495,357 B1 | 12/2002 | Fuglsang et al. |
| 6,512,941 B1 | 1/2003 | Weiss et al. |
| 6,514,415 B2 | 2/2003 | Hatch et al. |
| 6,551,843 B1 | 4/2003 | Rao et al. |
| 6,555,324 B1 | 4/2003 | Olweus et al. |
| 6,582,938 B1 | 6/2003 | Su et al. |
| 6,587,706 B1 | 7/2003 | Viswanathan |
| 6,594,517 B1 | 7/2003 | Nevo |
| 6,620,627 B1 | 9/2003 | Liberti et al. |
| 6,623,982 B1 | 9/2003 | Liberti et al. |
| 6,623,983 B1 | 9/2003 | Terstappen et al. |
| 6,645,731 B2 | 11/2003 | Terstappen et al. |
| 6,660,159 B1 | 12/2003 | Terstappen et al. |
| 6,696,838 B2 | 2/2004 | Raftery et al. |
| 6,700,379 B2 | 3/2004 | Peck et al. |
| 6,788,061 B1 | 9/2004 | Sweedler et al. |
| 6,790,366 B2 | 9/2004 | Terstappen et al. |
| 6,818,395 B1 | 11/2004 | Quake et al. |
| 6,822,454 B2 | 11/2004 | Peck et al. |
| 6,845,262 B2 | 1/2005 | Albert et al. |
| 6,858,384 B2 | 2/2005 | Terstappen et al. |
| 6,867,021 B2 | 3/2005 | Maes et al. |
| 6,876,200 B2 | 4/2005 | Anderson et al. |
| 6,890,426 B2 | 5/2005 | Terstappen et al. |
| 6,898,430 B1 | 5/2005 | Liberti et al. |
| 6,914,538 B2 | 7/2005 | Baird et al. |
| 6,958,609 B2 | 10/2005 | Raftery et al. |
| 7,011,794 B2 | 3/2006 | Kagan et al. |
| 7,056,657 B2 | 6/2006 | Terstappen et al. |
| 7,078,224 B1 | 7/2006 | Bitner et al. |
| 7,096,057 B2 | 8/2006 | Hockett et al. |
| 7,141,978 B2 | 11/2006 | Peck et al. |
| 7,169,560 B2 | 1/2007 | Lapidus et al. |
| 7,200,430 B2 | 4/2007 | Thomas et al. |
| 7,202,667 B2 | 4/2007 | Barbic |
| RE39,793 E | 8/2007 | Brenner |
| 7,271,592 B1 | 9/2007 | Gerald, II et al. |
| 7,274,191 B2 | 9/2007 | Park et al. |
| 7,282,180 B2 | 10/2007 | Tibbe et al. |
| 7,282,337 B1 | 10/2007 | Harris |
| 7,282,350 B2 | 10/2007 | Rao et al. |
| 7,304,478 B2 | 12/2007 | Tsuda et al. |
| 7,332,288 B2 | 2/2008 | Terstappen et al. |
| 7,345,479 B2 | 3/2008 | Park et al. |
| 7,393,665 B2 | 7/2008 | Brenner |
| 7,403,008 B2 | 7/2008 | Blank et al. |
| 7,405,567 B2 | 7/2008 | McDowell |
| 7,523,385 B2 | 4/2009 | Nguyen et al. |
| 7,537,897 B2 | 5/2009 | Brenner et al. |
| 7,544,473 B2 | 6/2009 | Brenner |
| 7,564,245 B2 | 7/2009 | Lee |
| 7,666,308 B2 | 2/2010 | Scholtens et al. |
| 7,688,777 B2 | 3/2010 | Liberti, Jr. et al. |
| 7,764,821 B2 | 7/2010 | Coumans et al. |
| 7,815,863 B2 | 10/2010 | Kagan et al. |
| 7,828,968 B2 | 11/2010 | Tibbe et al. |
| 7,863,012 B2 | 1/2011 | Rao et al. |
| 7,901,950 B2 | 3/2011 | Connelly et al. |
| 7,943,397 B2 | 5/2011 | Tibbe et al. |
| 8,067,938 B2 | 11/2011 | McDowell |
| 8,102,176 B2 | 1/2012 | Lee |
| 8,110,101 B2 | 2/2012 | Tibbe et al. |
| 8,111,669 B2 | 2/2012 | Liberti, Jr. et al. |
| 8,128,890 B2 | 3/2012 | Droog et al. |
| 8,841,104 B2 | 9/2014 | Dryga et al. |
| 8,889,368 B2 | 11/2014 | Barbreau et al. |
| 2001/0018192 A1 | 8/2001 | Terstappen et al. |
| 2002/0009759 A1 | 1/2002 | Terstappen et al. |
| 2002/0012669 A1 | 1/2002 | Presnell et al. |
| 2002/0098531 A1 | 7/2002 | Thacker |
| 2002/0130661 A1 | 9/2002 | Raftery et al. |
| 2002/0132228 A1 | 9/2002 | Terstappen et al. |
| 2002/0141913 A1 | 10/2002 | Terstappen et al. |
| 2002/0164629 A1 | 11/2002 | Quake et al. |
| 2002/0164659 A1 | 11/2002 | Rao et al. |
| 2002/0172987 A1 | 11/2002 | Terstappen et al. |
| 2003/0003441 A1 | 1/2003 | Colston et al. |
| 2003/0022231 A1 | 1/2003 | Wangh et al. |
| 2003/0054376 A1 | 3/2003 | Mullis et al. |
| 2003/0088181 A1 | 5/2003 | Gleich |
| 2003/0092029 A1 | 5/2003 | Josephson et al. |

(56) References Cited

U.S. PATENT DOCUMENTS

| | | |
|---|---|---|
| 2003/0129676 A1 | 7/2003 | Terstappen et al. |
| 2003/0203507 A1 | 10/2003 | Liberti et al. |
| 2003/0206577 A1 | 11/2003 | Liberti et al. |
| 2003/0222648 A1 | 12/2003 | Fan |
| 2004/0004043 A1 | 1/2004 | Terstappen et al. |
| 2004/0018611 A1 | 1/2004 | Ward et al. |
| 2004/0072269 A1 | 4/2004 | Rao et al. |
| 2004/0076990 A1 | 4/2004 | Picard et al. |
| 2004/0087032 A1 | 5/2004 | Chandler et al. |
| 2004/0101443 A1 | 5/2004 | Kagan et al. |
| 2004/0118757 A1 | 6/2004 | Terstappen et al. |
| 2004/0151629 A1 | 8/2004 | Pease et al. |
| 2005/0003464 A1 | 1/2005 | Tibbe et al. |
| 2005/0006990 A1 | 1/2005 | Williquette et al. |
| 2005/0026144 A1 | 2/2005 | Maes et al. |
| 2005/0043521 A1 | 2/2005 | Terstappen et al. |
| 2005/0069900 A1 | 3/2005 | Lentrichia |
| 2005/0079520 A1 | 4/2005 | Wu |
| 2005/0111414 A1 | 5/2005 | Liberti et al. |
| 2005/0128985 A1 | 6/2005 | Liberti et al. |
| 2005/0181353 A1 | 8/2005 | Rao et al. |
| 2005/0181463 A1 | 8/2005 | Rao et al. |
| 2005/0245814 A1 | 11/2005 | Anderson et al. |
| 2006/0019096 A1* | 1/2006 | Hatton .............. D01D 5/0007 428/364 |
| 2006/0024756 A1 | 2/2006 | Tibbe et al. |
| 2006/0115380 A1 | 6/2006 | Kagan et al. |
| 2006/0129327 A1 | 6/2006 | Kim et al. |
| 2006/0147901 A1 | 7/2006 | Jan et al. |
| 2006/0194192 A1 | 8/2006 | Rao et al. |
| 2006/0233712 A1 | 10/2006 | Penades et al. |
| 2006/0257847 A1 | 11/2006 | Scholtens et al. |
| 2006/0257945 A1 | 11/2006 | Masters et al. |
| 2006/0281094 A1 | 12/2006 | Squirrell et al. |
| 2007/0037173 A1 | 2/2007 | Allard et al. |
| 2007/0037231 A1 | 2/2007 | Sauer-Budge et al. |
| 2007/0090836 A1 | 4/2007 | Xiang et al. |
| 2007/0114181 A1 | 5/2007 | Li et al. |
| 2007/0116602 A1 | 5/2007 | Lee |
| 2007/0117158 A1 | 5/2007 | Coumans et al. |
| 2007/0152669 A1 | 7/2007 | Park et al. |
| 2007/0152670 A1 | 7/2007 | Park et al. |
| 2007/0154960 A1 | 7/2007 | Connelly et al. |
| 2007/0166835 A1 | 7/2007 | Bobrow et al. |
| 2007/0183935 A1 | 8/2007 | Clemmens et al. |
| 2007/0231926 A1 | 10/2007 | Ikeda |
| 2007/0296413 A1 | 12/2007 | Park et al. |
| 2008/0026451 A1 | 1/2008 | Braman et al. |
| 2008/0042650 A1 | 2/2008 | McDowell |
| 2008/0081330 A1 | 4/2008 | Kahvejian |
| 2008/0099715 A1 | 5/2008 | Adams et al. |
| 2008/0113350 A1 | 5/2008 | Terstappen |
| 2008/0199851 A1 | 8/2008 | Egan et al. |
| 2008/0204011 A1 | 8/2008 | Shoji |
| 2008/0204022 A1 | 8/2008 | Sillerud et al. |
| 2008/0241909 A1* | 10/2008 | Jung ................ G01N 33/54326 435/287.1 |
| 2008/0272788 A1 | 11/2008 | McDowell |
| 2008/0286838 A1 | 11/2008 | Yuan et al. |
| 2008/0315875 A1 | 12/2008 | Sillerud |
| 2009/0026082 A1 | 1/2009 | Rothberg et al. |
| 2009/0061456 A1 | 3/2009 | Allard et al. |
| 2009/0061476 A1 | 3/2009 | Tibbe et al. |
| 2009/0061477 A1 | 3/2009 | Tibbe et al. |
| 2009/0127589 A1 | 5/2009 | Rothberg et al. |
| 2009/0134869 A1 | 5/2009 | Lee |
| 2009/0136946 A1 | 5/2009 | Connelly et al. |
| 2009/0146658 A1 | 6/2009 | McDowell et al. |
| 2009/0148847 A1 | 6/2009 | Kokoris et al. |
| 2009/0156572 A1 | 6/2009 | Ikeura et al. |
| 2009/0173681 A1 | 7/2009 | Siddiqi |
| 2009/0191535 A1 | 7/2009 | Connelly et al. |
| 2009/0227044 A1 | 9/2009 | Dosev et al. |
| 2009/0246796 A1 | 10/2009 | Bernard et al. |
| 2009/0256572 A1 | 10/2009 | McDowell |
| 2009/0258365 A1 | 10/2009 | Terstappen et al. |
| 2009/0286264 A1 | 11/2009 | Scholtens et al. |
| 2010/0035252 A1 | 2/2010 | Rothberg et al. |
| 2010/0068723 A1 | 3/2010 | Jovanovich et al. |
| 2010/0072994 A1 | 3/2010 | Lee et al. |
| 2010/0129785 A1 | 5/2010 | Pris et al. |
| 2010/0137143 A1 | 6/2010 | Rothberg et al. |
| 2010/0144005 A1 | 6/2010 | Bin Kingombe et al. |
| 2010/0188073 A1 | 7/2010 | Rothberg et al. |
| 2010/0197507 A1 | 8/2010 | Rothberg et al. |
| 2010/0219824 A1 | 9/2010 | Sillerud et al. |
| 2010/0225315 A1 | 9/2010 | McDowell |
| 2010/0282617 A1 | 11/2010 | Rothberg et al. |
| 2010/0282788 A1 | 11/2010 | Liberti |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0326587 A1 | 12/2010 | Kagan et al. |
| 2011/0014686 A1 | 1/2011 | Tibbe et al. |
| 2011/0018538 A1 | 1/2011 | Lee |
| 2011/0044527 A1 | 2/2011 | Tibbe et al. |
| 2011/0046475 A1 | 2/2011 | Assif et al. |
| 2011/0052037 A1 | 3/2011 | Coumans et al. |
| 2011/0059444 A1 | 3/2011 | Stromberg et al. |
| 2011/0070586 A1 | 3/2011 | Slezak et al. |
| 2011/0086338 A1 | 4/2011 | Hwang et al. |
| 2011/0091987 A1 | 4/2011 | Weissleder et al. |
| 2011/0098623 A1 | 4/2011 | Lhang et al. |
| 2011/0104718 A1 | 5/2011 | Rao et al. |
| 2011/0183398 A1 | 7/2011 | Dasaratha et al. |
| 2011/0262893 A1 | 10/2011 | Dryga et al. |
| 2011/0262925 A1 | 10/2011 | Dryga et al. |
| 2011/0262926 A1 | 10/2011 | Esch et al. |
| 2011/0262927 A1 | 10/2011 | Dryga et al. |
| 2011/0262932 A1 | 10/2011 | Esch et al. |
| 2011/0262933 A1 | 10/2011 | Dryga et al. |
| 2011/0262989 A1 | 10/2011 | Clarizia et al. |
| 2011/0263833 A1 | 10/2011 | Dryga et al. |
| 2011/0300551 A1 | 12/2011 | Rao et al. |
| 2011/0301042 A1 | 12/2011 | Steinmann et al. |
| 2012/0045828 A1 | 2/2012 | Davis et al. |
| 2012/0094275 A1 | 4/2012 | Rao et al. |
| 2012/0100546 A1 | 4/2012 | Lowery, Jr. et al. |
| 2012/0112744 A1 | 5/2012 | McDowell et al. |
| 2013/0109590 A1 | 5/2013 | Clarizia et al. |
| 2013/0196341 A1 | 8/2013 | Neely et al. |
| 2013/0203634 A1 | 8/2013 | Jovanovich et al. |
| 2013/0316355 A1 | 11/2013 | Dryga et al. |
| 2014/0100136 A1 | 4/2014 | Clarizia et al. |
| 2014/0170021 A1 | 6/2014 | Dryga |
| 2014/0170639 A1 | 6/2014 | Marvell |
| 2014/0170640 A1 | 6/2014 | Dykes |
| 2014/0170641 A1 | 6/2014 | Macemon |
| 2014/0170652 A1 | 6/2014 | Sitdikov et al. |
| 2014/0170667 A1 | 6/2014 | Dykes et al. |
| 2014/0170669 A1 | 6/2014 | Vandervest |
| 2014/0170727 A1 | 6/2014 | Dryga et al. |
| 2014/0171340 A1 | 6/2014 | Dykes et al. |
| 2015/0212079 A1 | 7/2015 | Dryga et al. |

FOREIGN PATENT DOCUMENTS

| | | |
|---|---|---|
| WO | 89/06699 A1 | 7/1989 |
| WO | 90/08841 A1 | 8/1990 |
| WO | 91/02811 A1 | 3/1991 |
| WO | 92/08805 A1 | 5/1992 |
| WO | 92/15883 A1 | 9/1992 |
| WO | 95/31481 A1 | 11/1995 |
| WO | 98/20148 A1 | 5/1998 |
| WO | 99/53320 A1 | 10/1999 |
| WO | 01/73460 A1 | 10/2001 |
| WO | 02/98364 A2 | 12/2002 |
| WO | 2005/026762 A1 | 3/2005 |
| WO | 2005106480 A1 | 11/2005 |
| WO | 2007/018601 A1 | 2/2007 |
| WO | 2007/123345 A1 | 11/2007 |
| WO | 2007/135099 A1 | 11/2007 |
| WO | 2007123342 A1 | 11/2007 |

(56) References Cited

FOREIGN PATENT DOCUMENTS

| WO | 2008/119054 A1 | 10/2008 |
|---|---|---|
| WO | 2008/139419 A1 | 11/2008 |
| WO | 2009/048673 A2 | 4/2009 |
| WO | 2009/055587 A1 | 4/2009 |
| WO | 2009/122216 A1 | 10/2009 |
| WO | 2011/019874 A1 | 2/2011 |
| WO | 2011/133630 A1 | 10/2011 |
| WO | 2011/133632 A1 | 10/2011 |
| WO | 2011/133759 A1 | 10/2011 |
| WO | 2011/133760 A1 | 10/2011 |

OTHER PUBLICATIONS

Halbach, Design of Permanent Multipole Magnets with Oriented Rare Earth Cobalt Material, Nuclear Instrum Methods, 169:1-10 (1980).
Harada, et al., Monoclonal antibody G6K12 specific for membrane-associated differentiation marker of human stratified squamous epithelia and squamous cell carcinoma, J. Oral. Pathol. Med., 22(4):1145-152 (1993).
Harkins and Harrigan, "Labeling of Bacterial Pathogens for Flow Cytometric Detection and Enumeration" Curr Prot Cytom (2004) 11.17.1-11.17.20.
Harlow, et al., 1988, 'Antibodies', Cold Spring Harbor Laboratory, pp. 93-117.
Harris et al., Science 320:106-109 (2008).
Heijnen et al., 2009, Method for rapid detection of viable *Escherichia coli* in water using real-time NASBA, Water Research, 43:3124-3132.
Hijmans, et al., An immunofluorescence procedure for the detection of intracellular immunoglobulins, Clin. Exp. Immunol., 4:457 (1969).
Hinnisdales et al., Biotechniques Res., 19:4193 (1996).
Hirsch, et al., Easily reversible desthiobiotin binding to streptavidin, avidin, and other biotin-binding proteins: uses for protein labeling, detection, and isolation, Anal. Biochem., 208(2):343-57 (2002).
Hoult and Richards, The Signal-to-Noise Ratio of the Nuclear Magnetic Resonance Experiment, J. Magn. Reson., 24:71-85 (1976).
Hunter, et al., Immunoassays for Clinical Chemistry, pp. 147-162, Churchill Livingston, Edinborough (1983).
Inai, et al., Immunohistochemical detection of an enamel protein-related epitope in rat bone at an early state of osteogenesis, Histochemistry, 99(5):335-362 (1993).
International Search Report for PCT/US2013/076649 with an International filing date of Dec. 19, 2013, 2 pages.
International Search Report in PCT/US2011/33184, dated Jul. 25, 2011, 2 pages.
International Search Report in PCT/US2011/33186, dated Jun. 22, 2011, 1 page.
International Search Report in PCT/US2011/33410, dated Jul. 19, 2011, 2 pages.
International Search Report in PCT/US2011/33411, dated Jun. 22, 2011, 1 page.
International Search Report issued in PCT/US2013/076649, dated Feb. 27, 2014.
ISR and Written Opinion in PCT/US2008/058518, dated Sep. 29, 2009, 15 pages.
ISR and Written Opinion in PCT/US2008/058518, dated Jul. 7, 2008, 21 pages.
ISR and Written Opinion in PCT/US2008/062473, dated Oct. 29, 2008, 20 pages.
ISR and Written Opinion in PCT/US2008/080983, dated Mar. 3, 2009, 14 pages.
ISR and Written Opinion in PCT/US2009/067577, dated Feb. 5, 2010, 13 pages.
ISR and Written Opinion in PCT/US2011/48447, dated Dec. 22, 2011, 7 pages.
ISR and Written Opinion in PCT/US2011/48452, dated Dec. 22, 2011, 7 pages.

Johne, et al., *Staphylococcus aureus* exopolysaccharide in vivo demonstrated by immunomagnetic separation and electron microscopy, J. Clin. Microbiol. 27:1631-1635 (1989).
Johnson, Thermal Agitation of Electricity in Conductors, Phys. Rev., 32:97-109 (1928).
Kaittanis, et al., One-step nanoparticle mediated bacterial detection with magentic relaxation, Nano Lett., 7(2):381-383 (2007).
Klaschik, S., L. E. Lehmann, et al. (2002). "Real-time PCR for detection and differentiation of gram-positive and gram-negative bacteria." J Clin Microbial 40(11): 4304-4307.
Kleinstruer, "Microfluidics and Nanofluidics: Theory and Selected Applications," John Wiley & Sons, 2013.
Lecomte et al. Nucl Acids Res. 11:7505 (1983).
Lee, et al., Chip-NRM Biosensor for detection and molecular analysis of cells, Nature Medicine, 14(8):869-874 (2008).
Levin, Cell 88:5-8 (1997).
Li et al., 2010, Chemiluminescent Detect of *E. coli* O157:H7 Using Immunological Method Based on Magnetic Nanoparticles, J. of Nanoscience and Nanotechnology 10:696-701.
Life Technologies, "Dynabeads® for Immunoassay IVD", retrieved from http://www.invitrogen.com/site/us/en/home/Productsand-Services/Applications/Diagnostics-Clinical-Research/Bead-based-IVD-Assays/Bead-based-Immunoassay-IVD.html on May 29, 2013, four pages.
Lu et al., 2007, Magnetic Nanoparticles: Synthesis, Protection, Functionalization, and Application, Angew. Chem. Int. Ed. 46:1222-1244.
Lund, et al. Immunomagnetic separation and DNA hybridization for detection of enterotoxigenic *Escherichia coli* in a piglet model, J. Clin. Microbiol., 29:2259-2262 (1991).
Madonna A J, et al. "Detection of Bacteria from Biological Mixtures Using Immunomagnetic Separation Combined with Matrix-Assisted Laser Desorption/Ionization Time-of-flight Mass Spectrometry", Rapid Communications in Mass Spectrometry, John Wiley & Sons, GB, vol. 15, No. 13, Jan. 1, 2001, pp. 1068-1074.
Magin, et al., Miniature Magnetic Resonance Machines, IEEE Spectrum 34(10):51-61 (1997).
Malba, et al., Laser-lathe Lithography—A Novel Method for Manufacturing Nuclear Magnetic Resonance Microcoils, Biomed. Microdev., 5:21-27 (2003).
Maniatis et al., Molecular Cloning: A Laboratory Manual, 1982, Cold Spring Harbor, NY, pp. 280-281.
Margin, et al., High resolution microcoil 1H-NMR for mass-limited, nanoliter-volume samples, Science, 270:1967 (1995).
Margulies et al., Nature, 437: 376-380 (2005).
Massin, et al., Planar Microcoil-based magnetic resonance imaging of cells, Transducers '03, The 12th Int. Conf. on Solid State Sensors, Actuators, and Microsystems, Boston, Jun. 8-12, pp. 967-970 (2003).
Massin, et al., Planar Microcoil-based Microfluidic NMR Probes, J. Magn. Reson., 164:242-255 (2003).
Matar et al., 1990, Magnetic particles derived from iron nitride, IEEE Transactions on magnetics 26(1):60-62.
McDowell, et al., Low-Field Micro-Coil Probe Development for Portable NMR, 8th ICMRM, The Heidelberg Conference, Mibu, Japan, Aug. 22-26, 2005, Conference Program Abstract, 1 page.
McDowell, et al., Operating Nanoliter Scale NMR Microcoils in a Itesla Field, J. Mag. Reson., 188(1):74-82 (2007).
Abagram, Principles of Nuclear Magnetism, Carendon Press, Oxford, 1961, pp. 71-83.
Agrawal et al., 1990, Tetrahedron Letters 31:1543-46.
Andreassen, Jack, "One micron magnetic beads optimised for automated immunoassays" as Published in CLI Apr. 2005, retrieved from http://www.cli-online.com/uploads/tx_ttproducts/datasheet/one-micron-magnetic-beads-optimised-for-automatedimmunoassays.pdf on Dec. 28, 2015, four pages.
Armenean, et al., NMR Radiofrequency Microcoil Design: Electromagnetic Simulation Usefulness, Compes Rendus Biologies, 325(4):457-463 (2002).
Armenean, et al., Solenoidal and Planar Microcoils for NMR Spectroscopy, Proc. of the 25th Annual Int. Conf. of the IEEE Eng. in Med. and Bio. Soc., Cancun, Mexico, Sep. 17, 2003, pp. 3045-3048.

(56) References Cited

OTHER PUBLICATIONS

Barany et al., Gene, 108:1 (1991).
Barany F. (1991) PNAS 88:189-193.
Barany, F., Genome research, 1:5-16 (1991).
Behnia and Webb, Limited-Sample NMR Using Solenoidal Microcoils, Perfluorocarbon Plugs, and Capillary Spinning, Anal. Chem., 70:5326-5331 (1998).
Braslaysky et al., PNAS, 100:3690-3694 (2003).
Brown et al., Methods Enzymol., 68:109 (1979).
Bruno et al., "Development of an Immunomagnetic Assay System for Rapid Detection of Bacteria and Leukocytes in Body Fluids," J Mol Recog, 9 (1996) 474-479.
Burtis et al. (Burtis, C.A. (Ed.), Tietz Textbook of Clinical Chemistry, 3rd Edition (1999), W.B. Saunders Company, Philadelphia, PA, pp. 1793-1794).
Butter et al., 2002, Synthesis and properties of iron ferrofluids, J. Magn. Magn. Mater. 252:1-3.
Byrne, et al., Antibody-Based Sensors: Principles, Problems and Potential for Detection of Pathogens and Associated Toxins, Sensors, 9:4407-4445 (2009).
Campuzano, et al., Bacterial Isolation by Lectin Modified Microengines, Nano Lett. Jan. 11, 2012; 12(1): 396-401.
Cann et al., Proc. Natl. Acad. Sci. 95:14250 (1998).
Cariello et al., Nucl Acids Res, 19:4193 (1991).
Carroll, N. M., E. E. Jaeger, et al. (2000). "Detection of and discrimination between grampositive and gram-negative bacteria in intraocular samples by using nested PCR." J Clin 15 Microbial 38(5): 1753-1757.
Chandler et al., Automated immunomagnetic separation and microarray detection of E. Coli O157:H7 from poultry carcass rinse, Int. J. Food Micro., 70 (2001) 143-154.
Chapman, et al., Use of commercial enzyme immunoassays and immunomagnetic separation systems for detecting Escherichia coli O157 in bovine fecal samples, Applied and Environmental Microbiology, 63(7):2549-2553 (1997).
Cheng et al, 2012, Concentration and detection of bacteria in virtual environmental samples based on non-immunomagnetic separation and quantum dots by using a laboratory-made system, Proc. of SPIE:82310Y-1-82310Y-18.
Chien et al., J. Bacterial, 127:1550 (1976).
Chungang Wang et al. "Multifunctional Magnetic-OPtical Nanoparticle Probes for Simultaneous Detection, Separation, and Thermal Ablation of Multiple Pathogens", Small, vol. 6, No. 2 Jan. 18, 2010, pp. 283-289.
Ciobanu and Pennington, 3D Micron-scale MRI of Single Biological Cells, Solid State Nucl. Magn. Reson., 25:138-141 (2004).
Cold Spring Harbor Protocols, Recipe for Dulbecco's phosphate-buffered saline (Dulbecco's PBS, 2009, retrieved from http://cshprotocols.cshlp.Org/content/2009/3/pdb.rec11725. full?text_only=true on Mar. 9, 2015, one page.
Cooper et al., 2011, A micromagnetic flux concentrator device for isolation and visualization of pathogens. 15th International Conference on Miniaturized Systems for Chemistry and Life Sciences. Oct. 2-6, 2011, Seattle, Washington, USA.
Cross, et al., Choice of Bacteria in Animal Models of Sepsis, Infec. Immun. 61(7):2741-2747 (1983).
Dam et al. "Garlic (Allium sativum) Lectins Bind to High Mannose Oligosaccharide Chains", Journal of Biological Chemistry vol. 273, No. 10, Issue of Mar. 6, pp. 5528-5535, 1998.
Diaz et al., Braz J. Med. Res., 31:1239 (1998).
Djukovic, et al., Signal Enhancement in HPLC/Microcoil NMR Using Automated Column Trapping, Anal. Chem., 78:7154-7160 (2006).
DNA Replication 2nd edition, Kornberg and Baker, W.H. Freeman, New York, NY (1991).
Dover, Jason E., et al. "Recent advances in peptide probe-based biosensors for detection of infectious agents." Journal of microbiological methods 78.1 (2009): 10-19.
Drancourt, et al., Diagnosis of Mediterranean Spotted Fever by Indirect Immunofluorescence of Rickettsia conorii in Circulating Endothelial Cells Isolated with Monoclonal Antibody-Coated Immunomagnetic Beads, J. Infectious Diseases, 166(3):660-663, 1992.
Dynabeads® for Immunoassay IVD, retrieved from http://www.invitrogen.com/site/i3s/en/home/Products-and-Services/Applications/DiagnosticsClinical-Research/Bead-based-IVD-Assays/Bead-based-Immunoassay-iVD.html on May 29, 2013, four pages).
Elnifro, Elfath M. et al. "Multiplex PCR: optimization and application in diagnostic virology." Clinical Microbiology Reviews 13.4 (2000): 559-570.
Engvall, Enzyme immunoassay ELISA and EMIT, Meth. in Enzymol., 70:419-439 (1980).
Extended European Search Report issued in EP 11864030.9, dated Aug. 20, 2014.
Extended European Search Report, dated Oct. 15, 2013 for EP application No. 11772606.7.
Fan, et al., Self-assembly of ordered, robust, three-dimensional gold nanocrystal/silica arrays, Science, 304:567 (2004).
Fenwick et al., 1986, Mechanisms Involved in Protection Provided by Immunization against Core Lipopolysaccharides of Escherichia coli J5 from Lethal Haemophilus pleuropneumoniae Infections in Swine, Infection and Immunity 53 (2):298-304.
Fu, et al., Rapid Detection of Escherichia coli O157:H7 by Immunogmagnetic Separation and Real-time PCR, Int. J. Food Microbiology, 99(1):47-57, (2005).
Fukushima et al., Experimental Pulse NMR: A Nuts and Bolts Approach, Addison-Wesley, Reading, Mass., 1981.
Fung, M-C et al. PCR amplification of mRNA directly from a crude cell lysate prepared by thermophilic protease digestion, Nucleic Acids Research, vol. 19 (15), p. 4300, 1991.
Goding, J.W., Conjugation of antibodies with fluorochromes: modifications to the standard methods, J. Immunol. Meth., 13:215 (1976).
Goloshevsky, et al., Development of Low Field Nuclear Magnetic Resonance Microcoils, Rev. Sci. Inst.., 76:024101-1 to 024101-6 (2005).
Goloshevsky, et al., Integration of Biaxial Planar Gradient Coils and an RF Microcoil for NMR Flow Imaging, Meas. Sci. Technol., 16:505-512 (2005).
Grant, et al., Analysis of Multilayer Radio Frequency Microcoils for Nuclear Magnetic Resonance Spectroscopy, IEEE Trans. Magn., 37:2989-2998 (2001).
Grant, et al., NMR Spectroscopy of Single Neurons, Magn. Reson. Med., 44:19-22 (2000).
Griffiths et al., 1994, Isolation of high affinity human antibodies directly from large synthetic repertoires. EMBO J. 13 (14):3245-3260.
Minard, et al., Solenoidal Microcoil Design, Part I: Optimizing RF Homogeneity and coil dimensions, Concepts in Magn. Reson., 13(2):128-142 (2001).
Moreira et al., 2008, Detection of Salmonella typhimurium in Raw Meats using In-House Prepared Monoclonal Antibody Coated Magnetic Beads and PCR Assay of the fimA Gene. Journal of Immunoassay & Immunochemistry 29:58-69.
Moresi and Magin, Miniature Permanent Magnet for Table-top NMR, Concept. Magn. Res., 19B:35-43 (2003).
Moudrianakis et al., Proc. Natl. Acad. Sci. 53:564-71 (1965).
Mulder, et al., Characterization of two human monoclonal antibodies reactive with HLA-B12 and HLA-B60, respectively, raised by in vitro secondary immunization of peripheral blood lymphocytes, Hum. Immunol., 36 (3):186-192 (1993).
Myers and Gelfand, Biochemistry 30:7661 (1991).
Narang et al., Methods Enzymol., 68:90 (1979).
Nordstrom et al., J. Biol. Chem. 256:3112 (1981).
Nyquist, Thermal Agitation of Electrical Charge in Conductors, Phys. Rev., 32:110-113 (1928).
Ohno et al, 2011, Effects of Blood Group Antigen-Binding Adhesin Expression during Helicobacter pylori Infection of Mongolian Gerbils, The Journal of Infectious Diseases 203:726-735.
Olson, et al., High-resolution microcoil NMR for analysis of mass-limited, nanoliter samples, Anal. Chem., 70:645-650 (1998).
Olsvik_et_al_Magnetic_Seperation_Techniques_in_Diagnostic_Microbiology_Clinical_Microbiol_Rev_1994_7_43_54.

(56) References Cited

OTHER PUBLICATIONS

Pappas, et al., Cellular Separations: A Review of New Challenges in Analytical Chemistry, Analytica Chimica Acta, 601 (1):26-35 (2007).
Payne, M.J. et al., "The Use of Immobilized Lectins in the Separation of *Staphylococcus aureus, Escherichia Coli*, Listeria and *Salmonella* spp. from Pure Cultures and Foods", Journal of Applied Bacteriology, 1992, No. 73, pp. 41-52 (12 Pages).
Peck, et al., Design and Analysis of Microcoils for NMR Microscopy, J. Magn. Reson. B 108:114-124 (1995).
Peck, et al., RF Microcoils patterned using microlithographic techniques for use as microsensors in NMR, Proc. 15th Ann. Int. Conf. of the IEEE, Oct. 28-31, pp. 174-175 (1993).
Perez, et al., Viral-induced self-assembly of magnetic nanoparticle allows detection of viral particles in biological media, J. Am. Chem. Soc., 125:10192-10193 (2003).
Qiu, et al., Immunomagnetic separation and rapid detection of bacteria using bioluminescence and microfluidics, Talanta, 79:787-795 (2009).
Rogers, et al., Using microcontact printing to fabricate microcoils on capillaries for high resolution proton nuclear magnetic resonance on nanoliter volumes, Appl. Phys. Lett., 70:2464-2466 (1997).
Safarik et al., "The application of magnetic separations in applied Microbiology" Journal of Applied Bacteriology 1995, 78, 575-585.
Sambrook and Russell, Molecular Cloning: A Laboratory Manual 3Ed, Cold Spring Harbor Laboratory Press, 2001.
Seeber, et al., Design and Testing of high sensitivity Microreceiver Coil Apparatus for Nuclear Magnetic Resonance and Imaging, Rev. Sci. Inst., 72:2171-2179 (2001).
Seeber, et al., Triaxial Magnetic Field Gradient System for Microcoil Magnetic Resonance Imaging, Rev. Sci. Inst., 71:4263-4272 (2000).
Sillerud, et al., 1H NMR Detection of Superparamagnetic Nanoparticles at 1 T using a Microcoil and Novel Tuning Circuit, J. Magn. Reson. 181:181-190 (2006).
Sista et al., 2008, Heterogeneous Immunoassays Using Magnetic beads on a Digital Microfluidic Platform, Lab Chip 8 (2):2188-2196.
Skjerve, et al., Detection of Listeria monocytogenes in foods by immunomagnetic separation, Appl. Env. Microbiol., 56:3478 (1990).
Soni et al., Clin Chem 53:1996-2001 (2007).
Sorli, et al., Micro-spectrometer for NMR: analysis of small quantities in vitro, Meas. Sci. Technol., 15:877-880 (2004).
Stanley, Essentials in Immunology and Serology, Delmar, pp. 153-153 (2002).
Stauber, et al., Rapid generation of monoclonal antibody-secreting hybridomas against African horse sickness virus by in vitro immunization and the fusion/cloning technique, J. Immunol. Methods, 161(2):157-168 (1993).
Stenish and McGowan, Biochim Biophys Acta, 475:32 (1977).
Stocker, et al. Nanoliter volume, high-resolution NMR Microspectroscopy using a 60 um planer microcoil, IEEE Trans. Biomed. Eng., 44:1122-1127 (1997).
Subramanian, et al., RF Microcoil Design for Practical NMR of Mass-Limited Samples, J. Magn. Reson., 133:227-231 (1998).
Takagi et al., Appl. Environ. Microbial. 63:4504 (1997).
Taktak, et al., Multiparameter Magnetic Relaxation Switch Assays, Analytical Chemistry, 79(23):8863-8869 (2007).
The United States Naval Research Laboratory (NRL), "The FABS Device: Magnetic Particles", retrieved from http://www.nrl.navy.mil/chemistry/6170/6177/beads.php on Jan. 8, 2013, two pages.
Torensama, et al. Monoclonal Antibodies Specific for the Phase-Variant O-Acetylated Ki Capsule of *Escerichia coli*, J. Clin. Microbial., 29(7):1356-1358 (1991).
Trumbull, et al., Integrating microfabricated fluidic systems and NMR spectroscopy, IEEE Trans. Biomed. Eng., 47 (1):3-7 (2000).
Van Bentum, et al., Towards Nuclear Magnetic Resonance (MU)-Spectroscopy and (MU)-Imaging, Analyst, Royal Society of Chemistry, London, 129(9):793-803 (2004).
Vandeventer, J. Clin. Microbial. Jul. 2011, 49(7):2533-39.
Venkateswaran, et al., Production of Anti-Fibroblast Growth Factor Receptor Monoclonal Antibodies by In Vitro Immunization, Hybridoma, 11(6):729-739 (1992).
Verma, Biochim Biophys Acta. 473:1-38 (1977).
Vermunt, et al., Isolation of salmonelas by immunomagnetic separation, J. Appl. Bact., 72:112-118 (1992).
Wang and Irudayaraj, Multifunctional Magnetic-Optical Nanoparticle Probes for Simultaneous Detection, Separation, and Thermal Ablation of Multiple Pathogens, Small, 6(2):283-289 (2010).
Webb and Grant, Signal-to-Noise and Magnetic Susceptibility Trade-offs in Solenoidal Microcoils for NMR, J. Magn. Reson. B, 113:83-87 (1996).
Wensink, et al., High Signal to Noise Ratio in Low-field NMR on a Chip: Simulations and Experimental Results, 17th IEEE MEMS, 407-410 (2004).
Williams and Wang, Microfabrication of an electromagnetic power micro-relay using SU-8 based UV-LIGA technology, Microsystem Technologies, 10(10):699-705 (2004).
Wu, et al., 1H-NMR Spectroscopy on the Nanoliter Scale for Static and On-Line Measurements, Anal. Chem., 66:3849 (1994).
Yeung et al., 2002, Quantitative Screening of Yeast Surface-Displayed Polypeptide Libraries by Magnetic Bead Capture. Biotechnol. 18:212-220.
Yu et al. "Development of a Magnetic Microplate Chemifluorimmunoassay for Rapid Detection of Bacteria and Toxin in Blood", Analytical Biochemistry 261 (1998), pp. 1-7.

\* cited by examiner

ANALYZING BACTERIA WITHOUT CULTURING

RELATED APPLICATIONS

The present application is a continuation of U.S. patent application Ser. No. 13/091,548, filed Apr. 21, 2011, which claims the benefit of and priority to U.S. provisional patent application Ser. No. 61/326,588, filed Apr. 21, 2010, the contents of each of which are incorporated by reference herein in their entirety.

FIELD OF THE INVENTION

The invention generally relates to conducting an assay on a sample that isolates a pathogen from the sample and allows for analysis of the pathogen with minimal (i.e., at most 24 hrs of culturing) or no culturing of the pathogen.

BACKGROUND

Blood-borne pathogens are a significant healthcare problem. A delayed or improper diagnosis of a bacterial infection can result in sepsis—a serious, and often deadly, inflammatory response to the infection. Sepsis is the $10^{th}$ leading cause of death in the United States. Early detection of bacterial infections in blood is the key to preventing the onset of sepsis. Traditional methods of detection and identification of blood-borne infection include blood culture and antibiotic susceptibility assays. Those methods typically require culturing cells, which can be expensive and can take as long as 72 hours. Often, septic shock will occur before cell culture results can be obtained.

Alternative methods for detection of pathogens, particularly bacteria, have been described by others. Those methods include molecular detection methods, antigen detection methods, and metabolite detection methods. Molecular detection methods, whether involving hybrid capture or polymerase chain reaction (PCR), require high concentrations of purified DNA for detection. Both antigen detection and metabolite detection methods also require a relatively large amount of bacteria and have high limit of detection (usually $>10^4$ CFU/mL), thus requiring an enrichment step prior to detection. This incubation/enrichment period is intended to allow for the growth of bacteria and an increase in bacterial cell numbers to more readily aid in identification. In many cases, a series of two or three separate incubations is needed to isolate the target bacteria. However, such enrichment steps require a significant amount of time (e.g., at least a few days to a week) and can potentially compromise test sensitivity by killing some of the cells sought to be measured.

There is a need for methods for isolating target analytes, such as bacteria, from a sample, such as a blood sample, without an additional enrichment step. There is also a need for methods of isolating target analytes that are fast and sensitive in order to provide data for patient treatment decisions in a clinically relevant time frame.

SUMMARY

The present invention provides methods and devices for isolating pathogens in a biological sample. The invention allows the rapid detection of pathogen at very low levels in the sample; thus enabling early and accurate detection and identification of the pathogen. Since methods of the invention are able to isolate pathogens at very low levels, methods of the invention reduce or eliminate the culturing step that is typically associated with pathogen analysis and allow for more rapid analysis of the isolated pathogen. In this manner, methods of the invention provide data for patient treatment decisions in a clinically relevant time frame.

In certain aspects, methods of the invention involve obtaining a sample including a pathogen, conducting an assay that isolates the pathogen from the sample, culturing the isolated pathogen for at most about 24 hrs, and analyzing the pathogen. The invention may be carried out with magnetic particles having a target-specific binding moiety. Methods of the invention may involve introducing magnetic particles including a target-specific binding moiety to a body fluid sample in order to create a mixture, incubating the mixture to allow the particles to bind to a target, applying a magnetic field to capture target/magnetic particle complexes on a surface, and washing with a wash solution that reduces particle aggregation, thereby isolating target/magnetic particle complexes. A particular advantage of methods of the invention is for capture and isolation of bacteria and fungi directly from blood samples at low concentrations that are present in many clinical samples (as low as 1 CFU/ml of bacteria in a blood sample).

The target-specific binding moiety will depend on the target to be captured. The moiety may be any capture moiety known in the art, such as an antibody, an aptamer, a nucleic acid, a protein, a receptor, a phage or a ligand. In particular embodiments, the target-specific binding moiety is an antibody. In certain embodiments, the antibody is specific for bacteria. In other embodiments, the antibody is specific for fungi.

The target analyte refers to the target that will be captured and isolated by methods of the invention. The target may be bacteria, fungi, protein, a cell, a virus, a nucleic acid, a receptor, a ligand, or any molecule known in the art. In certain embodiments, the target is a pathogenic bacteria. In other embodiments, the target is a gram positive or gram negative bacteria. Exemplary bacterial species that may be captured and isolated by methods of the invention include *E. coli, Listeria, Clostridium, Mycobacterium, Shigella, Borrelia, Campylobacter, Bacillus, Salmonella, Staphylococcus, Enterococcus, Pneumococcus, Streptococcus*, and a combination thereof.

Methods of the invention may be performed with any type of magnetic particle. Magnetic particles generally fall into two broad categories. The first category includes particles that are permanently magnetizable, or ferromagnetic; and the second category includes particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction. In certain embodiments, the particles are superparamagnetic beads. In other embodiments, the magnetic particles include at least 70% superparamagnetic beads by weight. In certain embodiments, the superparamagnetic beads are from about 100 nm to about 250 nm in diameter. In certain embodiments, the magnetic particle is an iron-containing magnetic particle. In other embodiments, the magnetic particle includes iron oxide or iron platinum.

In certain embodiments, the incubating step includes incubating the mixture in a buffer that inhibits cell lysis. In certain embodiments, the buffer includes Tris(hydroximethyl)-aminomethane hydrochloride at a concentration of between about 50 mM and about 100 mM, preferably about 75 mM. In other embodiments, methods of the invention further include retaining the magnetic particles in a magnetic field during the washing step. Methods of the invention may be used with any body fluid. Exemplary body fluids include blood, sputum, serum, plasma, urine, saliva, sweat, and cerebral spinal fluid.

Another aspect of the invention provides methods for identifying a pathogen from a sample that involve obtaining a sample comprising a pathogen, conducting an assay that isolates the pathogen from the sample, and analyzing the pathogen without first culturing the pathogen.

Another aspect of the invention provides methods for identifying a pathogen from a sample that involve introducing magnetic particles comprising a target-specific binding moiety to a sample in order to create a mixture, incubating the mixture to allow the particles to bind to a pathogen in the sample, applying a magnetic field to isolate pathogen/magnetic particle complexes from the sample, culturing the isolated pathogen for at most about 24 hrs, and analyzing the pathogen.

DETAILED DESCRIPTION

The invention generally relates to conducting an assay on a sample that isolates a pathogen from the sample and allows for analysis of the pathogen with minimal (i.e., at most 24 hrs of culturing) or no culturing of the pathogen. In certain embodiments, methods of the invention involve obtaining a sample including a pathogen, conducting an assay that isolates the pathogen from the sample, culturing the isolated pathogen for at most about 24 hrs, and analyzing the pathogen. In other embodiments, culturing is for at most about 23 hrs, for at most about 22 hrs. for at most about 21 hrs, for at most about 20 hrs, for at most about 15 hrs, for at most about 10 hrs, for at most about 9 hrs, for at most about 8 hrs, for at most about 7 hrs, for at most about 6 hrs, for at most about 5 hrs, for at most about 4 hrs, for at most about 3 hrs, for at most about 2 hrs, or for at most about 1 hr. In particular embodiments, culturing is for less than 1 hr, for example, about 45 minutes, about 30 minutes, about 15 minutes, about 10 minutes, or for less than 10 minutes. In particular embodiments, culturing is completely eliminated and the isolated bacteria is analyzed directly without any culturing, i.e., culturing is eliminated.

In certain aspects, methods of the invention involve introducing magnetic particles including a target-specific binding moiety to a body fluid sample in order to create a mixture, incubating the mixture to allow the particles to bind to a target, applying a magnetic field to capture target/magnetic particle complexes on a surface, thereby isolating target/magnetic particle complexes. Methods of the invention may further involve washing the mixture in a wash solution that reduces particle aggregation. Certain fundamental technologies and principles are associated with binding magnetic materials to target entities and subsequently separating by use of magnet fields and gradients. Such fundamental technologies and principles are known in the art and have been previously described, such as those described in Janeway (Immunobiology, 6$^{th}$ edition, Garland Science Publishing), the content of which is incorporated by reference herein in its entirety.

Methods of the invention involve collecting a body fluid having a target analyte in a container, such as a blood collection tube (e.g., VACUTAINER, test tube specifically designed for venipuncture, commercially available from Becton, Dickinson and company). In certain embodiments, a solution is added that prevents or reduces aggregation of endogenous aggregating factors, such as heparin in the case of blood.

A body fluid refers to a liquid material derived from, for example, a human or other mammal. Such body fluids include, but are not limited to, mucus, blood, plasma, serum, serum derivatives, bile, phlegm, saliva, sweat, amniotic fluid, mammary fluid, urine, sputum, and cerebrospinal fluid (CSF), such as lumbar or ventricular CSF. A body fluid may also be a fine needle aspirate. A body fluid also may be media containing cells or biological material. In particular embodiments, the fluid is blood.

Methods of the invention may be used to detect any target analyte. The target analyte refers to the substance in the sample that will be captured and isolated by methods of the invention. The target may be bacteria, fungi, a protein, a cell (such as a cancer cell, a white blood cell a virally infected cell, or a fetal cell circulating in maternal circulation), a virus, a nucleic acid (e.g., DNA or RNA), a receptor, a ligand, a hormone, a drug, a chemical substance, or any molecule known in the art. In certain embodiments, the target is a pathogenic bacteria. In other embodiments, the target is a gram positive or gram negative bacteria. Exemplary bacterial species that may be captured and isolated by methods of the invention include *E. coli, Listeria, Clostridium, Mycobacterium, Shigella, Borrelia, Campylobacter, Bacillus, Salmonella, Staphylococcus, Enterococcus, Pneumococcus, Streptococcus*, and a combination thereof. A particular advantage of methods of the invention is for capture and isolation of bacteria and fungi directly from blood samples at low concentrations that are present in many clinical samples (as low as 1 CFU/ml of bacteria in a blood sample).

The sample is then mixed with magnetic particles having a particular magnetic moment and also including a target-specific binding moiety to generate a mixture that is allowed to incubate such that the particles bind to a target in the sample, such as a bacterium in a blood sample. The mixture is allowed to incubate for a sufficient time to allow for the particles to bind to the target analyte. The process of binding the magnetic particles to the target analytes associates a magnetic moment with the target analytes, and thus allows the target analytes to be manipulated through forces generated by magnetic fields upon the attached magnetic moment.

In general, incubation time will depend on the desired degree of binding between the target analyte and the magnetic beads (e.g., the amount of moment that would be desirably attached to the target), the amount of moment per target, the amount of time of mixing, the type of mixing, the reagents present to promote the binding and the binding chemistry system that is being employed. Incubation time can be anywhere from about 5 seconds to a few days. Exemplary incubation times range from about 10 seconds to about 2 hours. Binding occurs over a wide range of temperatures, generally between 15° C. and 40° C.

Methods of the invention may use any magnetic particulars. In certain embodiments, methods of the invention are performed with magnetic particle having a magnetic moment that allows for isolation of as low as 1 CFU/ml of bacteria in the sample. Production of magnetic particles is shown for example in Giaever (U.S. Pat. No. 3,970,518), Senyi et al. (U.S. Pat. No. 4,230,685), Dodin et al. (U.S. Pat.

No. 4,677,055), Whitehead et al. (U.S. Pat. No. 4,695,393), Benjamin et al. (U.S. Pat. No. 5,695,946), Giaever (U.S. Pat. No. 4,018,886), Rembaum (U.S. Pat. No. 4,267,234), Molday (U.S. Pat. No. 4,452,773), Whitehead et al. (U.S. Pat. No. 4,554,088), Forrest (U.S. Pat. No. 4,659,678), Liberti et al. (U.S. Pat. No. 5,186,827), Own et al. (U.S. Pat. No. 4,795,698), and Liberti et al. (WO 91/02811), the content of each of which is incorporated by reference herein in its entirety.

Magnetic particles generally fall into two broad categories. The first category includes particles that are permanently magnetizable, or ferromagnetic; and the second category includes particles that demonstrate bulk magnetic behavior only when subjected to a magnetic field. The latter are referred to as magnetically responsive particles. Materials displaying magnetically responsive behavior are sometimes described as superparamagnetic. However, materials exhibiting bulk ferromagnetic properties, e.g., magnetic iron oxide, may be characterized as superparamagnetic when provided in crystals of about 30 nm or less in diameter. Larger crystals of ferromagnetic materials, by contrast, retain permanent magnet characteristics after exposure to a magnetic field and tend to aggregate thereafter due to strong particle-particle interaction. In certain embodiments, the particles are superparamagnetic beads. In certain embodiments, the magnetic particle is an iron containing magnetic particle. In other embodiments, the magnetic particle includes iron oxide or iron platinum.

In certain embodiments, the magnetic particles include at least about 10% superparamagnetic beads by weight, at least about 20% superparamagnetic beads by weight, at least about 30% superparamagnetic beads by weight, at least about 40% superparamagnetic beads by weight, at least about 50% superparamagnetic beads by weight, at least about 60% superparamagnetic beads by weight, at least about 70% superparamagnetic beads by weight, at least about 80% superparamagnetic beads by weight, at least about 90% superparamagnetic beads by weight, at least about 95% superparamagnetic beads by weight, or at least about 99% superparamagnetic beads by weight. In a particular embodiment, the magnetic particles include at least about 70% superparamagnetic beads by weight.

In certain embodiments, the superparamagnetic beads are less than 100 nm in diameter. In other embodiments, the superparamagnetic beads are about 150 nm in diameter, are about 200 nm in diameter, are about 250 nm in diameter, are about 300 nm in diameter, are about 350 nm in diameter, are about 400 nm in diameter, are about 500 nm in diameter, or are about 1000 nm in diameter. In a particular embodiment, the superparamagnetic beads are from about 100 nm to about 250 nm in diameter.

In certain embodiments, the particles are beads (e.g., nanoparticles) that incorporate magnetic materials, or magnetic materials that have been functionalized, or other configurations as are known in the art. In certain embodiments, nanoparticles may be used that include a polymer material that incorporates magnetic material(s), such as nanometal material(s). When those nanometal material(s) or crystal(s), such as $Fe_3O_4$, are superparamagnetic, they may provide advantageous properties, such as being capable of being magnetized by an external magnetic field, and demagnetized when the external magnetic field has been removed. This may be advantageous for facilitating sample transport into and away from an area where the sample is being processed without undue bead aggregation.

One or more or many different nanometal(s) may be employed, such as $Fe_3O_4$, FePt, or Fe, in a core-shell configuration to provide stability, and/or various others as may be known in the art. In many applications, it may be advantageous to have a nanometal having as high a saturated moment per volume as possible, as this may maximize gradient related forces, and/or may enhance a signal associated with the presence of the beads. It may also be advantageous to have the volumetric loading in a bead be as high as possible, for the same or similar reason(s). In order to maximize the moment provided by a magnetizable nanometal, a certain saturation field may be provided. For example, for $Fe_3O_4$ superparamagnetic particles, this field may be on the order of about 0.3 T.

The size of the nanometal containing bead may be optimized for a particular application, for example, maximizing moment loaded upon a target, maximizing the number of beads on a target with an acceptable detectability, maximizing desired force-induced motion, and/or maximizing the difference in attached moment between the labeled target and non-specifically bound targets or bead aggregates or individual beads. While maximizing is referenced by example above, other optimizations or alterations are contemplated, such as minimizing or otherwise desirably affecting conditions.

In an exemplary embodiment, a polymer bead containing 80 wt % $Fe_3O_4$ superparamagnetic particles, or for example, 90 wt % or higher superparamagnetic particles, is produced by encapsulating superparamagnetic particles with a polymer coating to produce a bead having a diameter of about 250 nm.

Magnetic particles for use with methods of the invention have a target-specific binding moiety that allows for the particles to specifically bind the target of interest in the sample. The target-specific moiety may be any molecule known in the art and will depend on the target to be captured and isolated. Exemplary target-specific binding moieties include nucleic acids, proteins, ligands, antibodies, aptamers, and receptors.

In particular embodiments, the target-specific binding moiety is an antibody, such as an antibody that binds a particular bacterium. General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen, such the target bacteria, effective to produce an immune response. An exemplary protocol is as follows. The animal is injected with 100 milligrams of antigen resuspended in adjuvant, for example Freund's complete adjuvant, dependent on the size of the animal, followed three weeks later with a subcutaneous injection of 100 micrograms to 100 milligrams of immunogen with adjuvant dependent on the size of the animal, for example Freund's incomplete adjuvant. Additional subcutaneous or intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing protein G resin or target-specific affinity resin.

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4):145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

Any antibody or fragment thereof having affinity and specific for the bacteria of interest is within the scope of the invention provided herein. Immunomagnetic beads against *Salmonella* are provided in Vermunt et al. (J. Appl. Bact. 72:112, 1992). Immunomagnetic beads against *Staphylococcus aureus* are provided in Johne et al. (J. Clin. Microbiol. 27:1631, 1989). Immunomagnetic beads against *Listeria* are provided in Skjerve et al. (Appl. Env. Microbiol. 56:3478, 1990). Immunomagnetic beads against *Escherichia coli* are provided in Lund et al. (J. Clin. Microbiol. 29:2259, 1991).

Methods for attaching the target-specific binding moiety to the magnetic particle are known in the art. Coating magnetic particles with antibodies is well known in the art, see for example Harlow et al. (Antibodies, Cold Spring Harbor Laboratory, 1988), Hunter et al. (Immunoassays for Clinical Chemistry, pp. 147-162, eds., Churchill Livingston, Edinborough, 1983), and Stanley (Essentials in Immunology and Serology, Delmar, pp. 152-153, 2002). Such methodology can easily be modified by one of skill in the art to bind other types of target-specific binding moieties to the magnetic particles. Certain types of magnetic particles coated with a functional moiety are commercially available from Sigma-Aldrich (St. Louis, Mo.).

In certain embodiments, a buffer solution is added to the sample along with the magnetic beads. An exemplary buffer includes Tris(hydroximethyl)-aminomethane hydrochloride at a concentration of about 75 mM. It has been found that the buffer composition, mixing parameters (speed, type of mixing, such as rotation, shaking etc., and temperature) influence binding. It is important to maintain osmolality of the final solution (e.g., blood+buffer) to maintain high label efficiency. In certain embodiments, buffers used in methods of the invention are designed to prevent lysis of blood cells, facilitate efficient binding of targets with magnetic beads and to reduce formation of bead aggregates. It has been found that the buffer solution containing 300 mM NaCl, 75 mM Tris-HCl pH 8.0 and 0.1% Tween 20 meets these design goals.

Without being limited by any particular theory or mechanism of action, it is believed that sodium chloride is mainly responsible for maintaining osmolality of the solution and for the reduction of non-specific binding of magnetic bead through ionic interaction. Tris(hydroximethyl)-aminomethane hydrochloride is a well established buffer compound frequently used in biology to maintain pH of a solution. It has been found that 75 mM concentration is beneficial and sufficient for high binding efficiency. Likewise, Tween 20 is widely used as a mild detergent to decrease nonspecific attachment due to hydrophobic interactions. Various assays use Tween 20 at concentrations ranging from 0.01% to 1%. The 0.1% concentration appears to be optimal for the efficient labeling of bacteria, while maintaining blood cells intact.

An alternative approach to achieve high binding efficiency while reducing time required for the binding step is to use static mixer, or other mixing devices that provide efficient mixing of viscous samples at high flow rates, such as at or around 5 mL/min. In one embodiment, the sample is mixed with binding buffer in ratio of, or about, 1:1, using a mixing interface connector. The diluted sample then flows through a mixing interface connector where it is mixed with target-specific nanoparticles. Additional mixing interface connectors providing mixing of sample and antigen-specific nanoparticles can be attached downstream to improve binding efficiency. The combined flow rate of the labeled sample is selected such that it is compatible with downstream processing.

After binding of the magnetic particles to the target analyte in the mixture to form target/magnetic particle complexes, a magnetic field is applied to the mixture to capture the complexes on a surface. Components of the mixture that are not bound to magnetic particles will not be affected by the magnetic field and will remain free in the mixture. Methods and apparatuses for separating target/magnetic particle complexes from other components of a mixture are known in the art. For example, a steel mesh may be coupled to a magnet, a linear channel or channels may be configured with adjacent magnets, or quadrapole magnets with annular flow may be used. Other methods and apparatuses for separating target/magnetic particle complexes from other components of a mixture are shown in Rao et al. (U.S. Pat. No. 6,551,843), Liberti et al. (U.S. Pat. No. 5,622,831), Hatch et al. (U.S. Pat. No. 6,514,415), Benjamin et al. (U.S. Pat. No. 5,695,946), Liberti et al. (U.S. Pat. No. 5,186,827), Wang et al. (U.S. Pat. No. 5,541,072), Liberti et al. (U.S. Pat. No. 5,466,574), and Terstappen et al. (U.S. Pat. No. 6,623,983), the content of each of which is incorporated by reference herein in its entirety.

In certain embodiments, the magnetic capture is achieved at high efficiency by utilizing a flow-through capture cell with a number of strong rare earth bar magnets placed perpendicular to the flow of the sample. When using a flow chamber with flow path cross-section 0.5 mm×20 mm (h×w) and 7 bar NdFeB magnets, the flow rate could be as high as 5 mL/min or more, while achieving capture efficiency close to 100%.

The above described type of magnetic separation produces efficient capture of a target analyte and the removal of a majority of the remaining components of a sample mixture. However, such a process may produce a sample that contains a percent of magnetic particles that are not bound to target analytes, as well as non-specific target entities. Non-specific target entities may for example be bound at a much lower efficiency, for example 1% of the surface area, while a target of interest might be loaded at 50% or nearly 100% of the available surface area or available antigenic cites. However, even 1% loading may be sufficient to impart force necessary for trapping in a magnetic gradient flow cell or sample chamber.

The presence of magnetic particles that are not bound to target analytes and non-specific target entities on the surface that includes the target/magnetic particle complexes may interfere with the ability to successfully detect the target of interest. The magnetic capture of the resulting mix, and close contact of magnetic particles with each other and bound targets, result in the formation of aggregate that is hard to dispense and which might be resistant or inadequate for subsequent processing or analysis steps. In order to remove magnetic particles that are not bound to target analytes and non-specific target entities, methods of the invention may further involve washing the surface with a wash solution that reduces particle aggregation, thereby isolating target/magnetic particle complexes from the magnetic particles that are not bound to target analytes and non-specific target entities. The wash solution minimizes the formation of the aggregates.

Methods of the invention may use any wash solution that imparts a net negative charge to the magnetic particle that is not sufficient to disrupt interaction between the target-specific moiety of the magnetic particle and the target analyte. Without being limited by any particular theory or mechanism of action, it is believed that attachment of the negatively charged molecules in the wash solution to magnetic particles provides net negative charge to the particles and facilitates dispersal of non-specifically aggregated particles. At the same time, the net negative charge is not sufficient to disrupt strong interaction between the target-specific moiety of the magnetic particle and the target analyte (e.g., an antibody-antigen interaction). Exemplary solutions include heparin, Tris-HCl, Tris-borate-EDTA (TBE), Tris-acetate-EDTA (TAE), Tris-cacodylate, HEPES (4-(2-hydroxyethyl)-1-piperazineethanesulphonic acid), PBS (phosphate buffered saline), PIPES (piperazine-N,N'-bis(2-ethanesulfonic acid), MES (2-N-morpholino)ethanesulfonic acid), Tricine (N-(Tri(hydroxymethyl)methyl)glycine), and similar buffering agents. In certain embodiments, only a single wash cycle is performed. In other embodiments, more than one wash cycle is performed.

In particular embodiments, the wash solution includes heparin. For embodiments in which the body fluid sample is blood, the heparin also reduces probability of clotting of blood components after magnetic capture. The bound targets are washed with heparin-containing buffer 1-3 times to remove blood components and to reduce formation of aggregates.

Since methods of the invention are able to isolate pathogens at very low levels, methods of the invention reduce or eliminate the culturing step that is typically associated with pathogen analysis and allow for more rapid analysis of the isolated pathogen. Reduced culturing refers to culturing for at most about 24 hrs, for example, for at most about 23 hrs, for at most about 22 hrs, for at most about 21 hrs, for at most about 20 hrs, for at most about 15 hrs, for at most about 10 hrs, for at most about 9 hrs, for at most about 8 hrs, for at most about 7 hrs, for at most about 6 hrs, for at most about 5 hrs, for at most about 4 hrs, for at most about 3 hrs, for at most about 2 hrs, or for at most about 1 hr. In particular embodiments, culturing is for less than 1 hr, for example, about 45 minutes, about 30 minutes, about 15 minutes, about 10 minutes, or for less than 10 minutes. In particular embodiments, culturing is completely eliminated and the isolated bacteria is analyzed directly without any culturing, i.e., culturing is eliminated.

The target may be analyzed by a multitude of existing technologies, such as miniature NMR, Polymerase Chain Reaction (PCR), mass spectrometry, fluorescent labeling and visualization using microscopic observation, fluorescent in situ hybridization (FISH), growth-based antibiotic sensitivity tests, and variety of other methods that may be conducted with purified target without significant contamination from other sample components. In one embodiment, isolated bacteria are lysed with a chaotropic solution, and DNA is bound to DNA extraction resin. After washing of the resin, the bacterial DNA is eluted and used in quantitative RT-PCR to detect the presence of a specific species, and/or, subclasses of bacteria.

In another embodiment, captured bacteria is removed from the magnetic particles to which they are bound and the processed sample is mixed with fluorescent labeled antibodies specific to the bacteria or fluorescent Gram stain. After incubation, the reaction mixture is filtered through 0.2 μm to 1.0 μm filter to capture labeled bacteria while allowing majority of free beads and fluorescent labels to pass through the filter. Bacteria is visualized on the filter using microscopic techniques, e.g. direct microscopic observation, laser scanning or other automated methods of image capture. The presence of bacteria is detected through image analysis. After the positive detection by visual techniques, the bacteria can be further characterized using PCR or genomic methods.

Detection of bacteria of interest can be performed by use of nucleic acid probes following procedures which are known in the art. Suitable procedures for detection of bacteria using nucleic acid probes are described, for example, in Stackebrandt et al. (U.S. Pat. No. 5,089,386), King et al. (WO 90/08841), Foster et al. (WO 92/15883), and Cossart et al. (WO 89/06699), each of which is hereby incorporated by reference.

A suitable nucleic acid probe assay generally includes sample treatment and lysis, hybridization with selected probe(s), hybrid capture, and detection. Lysis of the bacteria is necessary to release the nucleic acid for the probes. The nucleic acid target molecules are released by treatment with any of a number of lysis agents, including alkali (such as NaOH), guanidine salts (such as guanidine thiocyanate), enzymes (such as lysozyme, mutanolysin and proteinase K), and detergents. Lysis of the bacteria, therefore, releases both DNA and RNA, particularly ribosomal RNA and chromosomal DNA both of which can be utilized as the target molecules with appropriate selection of a suitable probe. Use of rRNA as the target molecule(s), may be advantageous because rRNAs constitute a significant component of cellular mass, thereby providing an abundance of target molecules. The use of rRNA probes also enhances specificity for the bacteria of interest, that is, positive detection without undesirable cross-reactivity which can lead to false positives or false detection.

Hybridization includes addition of the specific nucleic acid probes. In general, hybridization is the procedure by which two partially or completely complementary nucleic acids are combined, under defined reaction conditions, in an anti-parallel fashion to form specific and stable hydrogen bonds. The selection or stringency of the hybridization/reaction conditions is defined by the length and base composition of the probe/target duplex, as well as by the level and geometry of mis-pairing between the two nucleic acid strands. Stringency is also governed by such reaction parameters as temperature, types and concentrations of denaturing agents present and the type and concentration of ionic species present in the hybridization solution.

The hybridization phase of the nucleic acid probe assay is performed with a single selected probe or with a combination of two, three or more probes. Probes are selected having sequences which are homologous to unique nucleic acid sequences of the target organism. In general, a first capture probe is utilized to capture formed hybrid molecules. The hybrid molecule is then detected by use of antibody reaction or by use of a second detector probe which may be labelled with a radioisotope (such as phosphorus-32) or a fluorescent label (such as fluorescein) or chemiluminescent label.

Detection of bacteria of interest can also be performed by use of PCR techniques. A suitable PCR technique is described, for example, in Verhoef et al. (WO 92/08805). Such protocols may be applied directly to the bacteria captured on the magnetic beads. The bacteria is combined with a lysis buffer and collected nucleic acid target molecules are then utilized as the template for the PCR reaction.

For detection of the selected bacteria by use of antibodies, isolated bacteria are contacted with antibodies specific to the bacteria of interest. As noted above, either polyclonal or monoclonal antibodies can be utilized, but in either case have affinity for the particular bacteria to be detected. These antibodies, will adhere/bind to material from the specific target bacteria. With respect to labeling of the antibodies, these are labeled either directly or indirectly with labels used in other known immunoassays. Direct labels may include fluorescent, chemiluminescent, bioluminescent, radioactive, metallic, biotin or enzymatic molecules. Methods of combining these labels to antibodies or other macromolecules are well known to those in the art. Examples include the methods of Hijmans, W. et al. (1969), Clin. Exp. Immunol. 4, 457-, for fluorescein isothiocyanate, the method of Goding, J. W. (1976), J. Immunol. Meth. 13, 215-, for tetramethylrhodamine isothiocyanate, and the method of Ingrall, E. (1980), Meth. in Enzymol. 70, 419-439 for enzymes.

These detector antibodies may also be labeled indirectly. In this case the actual detection molecule is attached to a secondary antibody or other molecule with binding affinity for the anti-bacteria cell surface antibody. If a secondary antibody is used it is preferably a general antibody to a class of antibody (IgG and IgM) from the animal species used to raise the anti-bacteria cell surface antibodies. For example, the second antibody may be conjugated to an enzyme, either alkaline phosphatase or to peroxidase. To detect the label, after the bacteria of interest is contacted with the second antibody and washed, the isolated component of the sample is immersed in a solution containing a chromogenic substrate for either alkaline phosphatase or peroxidase. A chromogenic substrate is a compound that can be cleaved by an enzyme to result in the production of some type of detectable signal which only appears when the substrate is cleaved from the base molecule. The chromogenic substrate is colorless, until it reacts with the enzyme, at which time an intensely colored product is made. Thus, material from the bacteria colonies adhered to the membrane sheet will become an intense blue/purple/black color, or brown/red while material from other colonies will remain colorless. Examples of detection molecules include fluorescent substances, such as 4-methylumbelliferyl phosphate, and chromogenic substances, such as 4-nitrophenylphosphate, 3,3', 5,5'-tetramethylbenzidine and 2,2'-azino-di-[3-ethelbenzthiazoliane sulfonate (6)]. In addition to alkaline phosphatase and peroxidase, other useful enzymes include β-galactosidase, β-glucuronidase, α-glucosidase, β-glucosidase, α-mannosidase, galactose oxidase, glucose oxidase and hexokinase.

Detection of bacteria of interest using NMR may be accomplished as follows. In the use of NMR as a detection methodology, in which a sample is delivered to a detector coil centered in a magnet, the target of interest, such as a magnetically labeled bacterium, may be delivered by a fluid medium, such as a fluid substantially composed of water. In such a case, the magnetically labeled target may go from a region of very low magnetic field to a region of high magnetic field, for example, a field produced by an about 1 to about 2 Tesla magnet. In this manner, the sample may traverse a magnetic gradient, on the way into the magnet and on the way out of the magnet. As may be seen via equations 1 and 2 below, the target may experience a force pulling into the magnet in the direction of sample flow on the way into the magnet, and a force into the magnet in the opposite direction of flow on the way out of the magnet. The target may experience a retaining force trapping the target in the magnet if flow is not sufficient to overcome the gradient force.

$$m \cdot (\text{del } B) = F \quad \text{Equation 1}$$

$$v_t = -F/(6 * p * n * r) \quad \text{Equation 2}$$

where n is the viscosity, r is the bead diameter, F is the vector force, B is the vector field, and m is the vector moment of the bead.

Magnetic fields on a path into a magnet may be non-uniform in the transverse direction with respect to the flow into the magnet. As such, there may be a transverse force that pulls targets to the side of a container or a conduit that provides the sample flow into the magnet. Generally, the time it takes a target to reach the wall of a conduit is associated with the terminal velocity and is lower with increasing viscosity. The terminal velocity is associated with the drag force, which may be indicative of creep flow in certain cases. In general, it may be advantageous to have a high viscosity to provide a higher drag force such that a target will tend to be carried with the fluid flow through the magnet without being trapped in the magnet or against the conduit walls.

Newtonian fluids have a flow characteristic in a conduit, such as a round pipe, for example, that is parabolic, such that the flow velocity is zero at the wall, and maximal at the center, and having a parabolic characteristic with radius. The velocity decreases in a direction toward the walls, and it is easier to magnetically trap targets near the walls, either with transverse gradients force on the target toward the conduit wall, or in longitudinal gradients sufficient to prevent target flow in the pipe at any position. In order to provide favorable fluid drag force to keep the samples from being trapped in the conduit, it may be advantageous to have a plug flow condition, wherein the fluid velocity is substantially uniform as a function of radial position in the conduit.

When NMR detection is employed in connection with a flowing sample, the detection may be based on a perturbation of the NMR water signal caused by a magnetically labeled target (Sillerud et al., JMR (Journal of Magnetic Resonance), vol. 181, 2006). In such a case, the sample may be excited at time 0, and after some delay, such as about 50 ms or about 100 ms, an acceptable measurement (based on a detected NMR signal) may be produced. Alternatively, such a measurement may be produced immediately after excitation, with the detection continuing for some duration, such as about 50 ms or about 100 ms. It may be advantageous to detect the NMR signal for substantially longer time durations after the excitation.

By way of example, the detection of the NMR signal may continue for a period of about 2 seconds in order to record spectral information at high-resolution. In the case of parabolic or Newtonian flow, the perturbation excited at time 0 is typically smeared because the water around the perturbation source travels at different velocity, depending on radial position in the conduit. In addition, spectral information may be lost due to the smearing or mixing effects of the differential motion of the sample fluid during signal detection. When carrying out an NMR detection application involving a flowing fluid sample, it may be advantageous to provide plug-like sample flow to facilitate desirable NMR contrast and/or desirable NMR signal detection.

Differential motion within a flowing Newtonian fluid may have deleterious effects in certain situations, such as a situation in which spatially localized NMR detection is desired, as in magnetic resonance imaging. In one example, a magnetic object, such as a magnetically labeled bacterium, is flowed through the NMR detector and its presence and location are detected using MRI techniques. The detection may be possible due to the magnetic field of the magnetic object, since this field perturbs the magnetic field of the fluid in the vicinity of the magnetic object. The detection of the magnetic object is improved if the fluid near the object remains near the object. Under these conditions, the magnetic perturbation may be allowed to act longer on any given volume element of the fluid, and the volume elements of the fluid so affected will remain in close spatial proximity. Such a stronger, more localized magnetic perturbation will be more readily detected using NMR or MRI techniques.

If a Newtonian fluid is used to carry the magnetic objects through the detector, the velocity of the fluid volume elements will depend on radial position in the fluid conduit. In such a case, the fluid near a magnetic object will not remain near the magnetic object as the object flows through the detector. The effect of the magnetic perturbation of the object on the surrounding fluid may be smeared out in space, and the strength of the perturbation on any one fluid volume element may be reduced because that element does not stay within range of the perturbation. The weaker, less-well-localized perturbation in the sample fluid may be undetectable using NMR or MRI techniques.

Certain liquids, or mixtures of liquids, exhibit non-parabolic flow profiles in circular conduits. Such fluids may exhibit non-Newtonian flow profiles in other conduit shapes. The use of such a fluid may prove advantageous as the detection fluid in an application employing an NMR-based detection device. Any such advantageous effect may be attributable to high viscosity of the fluid, a plug-like flow profile associated with the fluid, and/or other characteristic(s) attributed to the fluid that facilitate detection. As an example, a shear-thinning fluid of high viscosity may exhibit a flow velocity profile that is substantially uniform across the central regions of the conduit cross-section. The velocity profile of such a fluid may transition to a zero or very low value near or at the walls of the conduit, and this transition region may be confined to a very thin layer near the wall.

Not all fluids, or all fluid mixtures, are compatible with the NMR detection methodology. In one example, a mixture of glycerol and water can provide high viscosity, but the NMR measurement is degraded because separate NMR signals are detected from the water and glycerol molecules making up the mixture. This can undermine the sensitivity of the NMR detector. In another example, the non-water component of the fluid mixture can be chosen to have no NMR signal, which may be achieved by using a perdeuterated fluid component, for example, or using a perfluorinated fluid component. This approach may suffer from the loss of signal intensity since a portion of the fluid in the detection coil does not produce a signal.

Another approach may be to use a secondary fluid component that constitutes only a small fraction of the total fluid mixture. Such a low-concentration secondary fluid component can produce an NMR signal that is of negligible intensity when compared to the signal from the main component of the fluid, which may be water. It may be advantageous to use a low-concentration secondary fluid component that does not produce an NMR signal in the detector. For example, a perfluorinated or perdeuterated secondary fluid component may be used. The fluid mixture used in the NMR detector may include one, two, or more than two secondary components in addition to the main fluid component. The fluid components employed may act in concert to produce the desired fluid flow characteristics, such as high-viscosity and/or plug flow. The fluid components may be useful for providing fluid characteristics that are advantageous for the performance of the NMR detector, for example by providing NMR relaxation times that allow faster operation or higher signal intensities.

A non-Newtonian fluid may provide additional advantages for the detection of objects by NMR or MRI techniques. As one example, the objects being detected may all have substantially the same velocity as they go through the detection coil. This characteristic velocity may allow simpler or more robust algorithms for the analysis of the detection data. As another example, the objects being detected may have fixed, known, and uniform velocity. This may prove advantageous in devices where the position of the detected object at later times is needed, such as in a device that has a sequestration chamber or secondary detection chamber down-stream from the NMR or MRI detection coil, for example.

In an exemplary embodiment, sample delivery into and out of a 1.7 T cylindrical magnet using a fluid delivery medium containing 0.1% to 0.5% Xanthan gum in water was successfully achieved. Such delivery is suitable to provide substantially plug-like flow, high viscosity, such as from about 10 cP to about 3000 cP, and good NMR contrast in relation to water. Xanthan gum acts as a non-Newtonian fluid, having characteristics of a non-Newtonian fluid that are well know in the art, and does not compromise NMR signal characteristics desirable for good detection in a desirable mode of operation.

In certain embodiments, methods of the invention are useful for direct detection of bacteria from blood. Such a process is described here. Sample is collected in sodium heparin tube by venipuncture, acceptable sample volume is about 1 mL to 10 mL. Sample is diluted with binding buffer and superparamagnetic particles having target-specific binding moieties are added to the sample, followed by incubation on a shaking incubator at 37° C. for about 30 min to 120 min. Alternative mixing methods can also be used. In a particular embodiment, sample is pumped through a static mixer, such that reaction buffer and magnetic beads are added to the sample as the sample is pumped through the mixer. This process allows for efficient integration of all components into a single fluidic part, avoids moving parts and separate incubation vessels and reduces incubation time.

Capture of the labeled targets allows for the removal of blood components and reduction of sample volume from 30 mL to 5 mL. The capture is performed in a variety of magnet/flow configurations. In certain embodiments, methods include capture in a sample tube on a shaking platform or capture in a flow-through device at flow rate of 5 mL/min, resulting in total capture time of 6 min.

After capture, the sample is washed with wash buffer including heparin to remove blood components and free beads. The composition of the wash buffer is optimized to reduce aggregation of free beads, while maintaining the integrity of the bead/target complexes.

The detection method is based on a miniature NMR detector tuned to the magnetic resonance of water. When the sample is magnetically homogenous (no bound targets), the NMR signal from water is clearly detectable and strong. The presence of magnetic material in the detector coil disturbs the magnetic field, resulting in reduction in water signal. One of the primary benefits of this detection method is that there is no magnetic background in biological samples which significantly reduces the requirements for stringency of sample processing. In addition, since the detected signal is generated by water, there is a built-in signal amplification which allows for the detection of a single labeled bacterium.

This method provides for isolation and detection of as low as or even lower than 1 CFU/ml of bacteria in a blood sample.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Sample

Blood samples from healthy volunteers were spiked with clinically relevant concentrations of bacteria (1-10 CFU/mL) including both laboratory strains and clinical isolates of the bacterial species most frequently found in bloodstream infections.

Example 2: Antibody Preparation

In order to generate polyclonal, pan-Gram-positive bacteria-specific IgG, a goat was immunized by first administering bacterial antigens suspended in complete Freund's adjuvant intra lymph node, followed by subcutaneous injection of bacterial antigens in incomplete Freund's adjuvant in 2 week intervals. The antigens were prepared for antibody production by growing bacteria to exponential phase ($OD_{600}$=0.4-0.8). Following harvest of the bacteria by centrifugation, the bacteria was inactivated using formalin fixation in 4% formaldehyde for 4 hr at 37° C. After 3 washes of bacteria with PBS (15 min wash, centrifugation for 20 min at 4000 rpm) the antigen concentration was measured using BCA assay and the antigen was used at 1 mg/mL for immunization. In order to generate Gram-positive bacteria-specific IgG, several bacterial species were used for inoculation: *Staphylococcus aureus, Staphylococcus epidermidis, Enterococcus faecium* and *Enterococcus fecalis*.

The immune serum was purified using affinity chromatography on a protein G sepharose column (GE Healthcare), and reactivity was determined using ELISA. Antibodies cross-reacting with Gram-negative bacteria and fungi were removed by absorption of purified IgG with formalin-fixed Gram-negative bacteria and fungi. The formalin-fixed organisms were prepared similar to as described above and mixed with IgG. After incubation for 2 hrs at room temperature, the preparation was centrifuged to remove bacteria. Final antibody preparation was clarified by centrifugation and used for the preparation of antigen-specific magnetic beads.

Example 3: Preparation of Antigen-Specific Magnetic Beads

Superparamagnetic beads were synthesized by encapsulating iron oxide nanoparticles (5-15 nm diameter) in a latex core and labeling with goat IgG. Ferrofluid containing nanoparticles in organic solvent was precipitated with ethanol, nanoparticles were resuspended in aqueous solution of styrene and surfactant Hitenol BC-10, and emulsified using sonication. The mixture was allowed to equilibrate overnight with stirring and filtered through 1.2 and 0.45 μm filters to achieve uniform micelle size. Styrene, acrylic acid and divynilbenzene were added in carbonate buffer at pH 9.6. The polymerization was initiated in a mixture at 70° C. with the addition of $K_2S_2O_8$ and the reaction was allowed to complete overnight. The synthesized particles were washed 3 times with 0.1% SDS using magnetic capture, filtered through 1.2, 0.8, and 0.45 μm filters and used for antibody conjugation.

The production of beads resulted in a distribution of sizes that may be characterized by an average size and a standard deviation. In the case of labeling and extracting of bacteria from blood, the average size for optimal performance was found to be between 100 and 350 nm, for example between 200 nm to 250 nm.

The purified IgG were conjugated to prepared beads using standard chemistry. After conjugation, the beads were resuspended in 0.1% BSA which is used to block non-specific binding sites on the bead and to increase the stability of bead preparation.

Example 4: Labeling of Rare Cells Using Excess of Magnetic Nanoparticles

Bacteria, present in blood during blood-stream infection, were magnetically labeled using the superparamagnetic beads prepared in Example 3 above. The spiked samples as described in Example 1 were diluted 3-fold with a Tris-based binding buffer and target-specific beads, followed by incubation on a shaking platform at 37° C. for up to 2 hr. After incubation, the labeled targets were magnetically separated followed by a wash step designed to remove blood products. See example 5 below.

Example 5: Magnetic Capture of Bound Bacteria

Blood including the magnetically labeled target bacteria and excess free beads were injected into a flow-through capture cell with a number of strong rare earth bar magnets placed perpendicular to the flow of the sample. With using a flow chamber with flow path cross-section 0.5 mm×20 mm (h×w) and 7 bar NdFeB magnets, a flow rate as high as 5 mL/min was achieved. After flowing the mixture through the channel in the presence of the magnet, a wash solution including heparin was flowed through the channel. The bound targets were washed with heparin-containing buffer one time to remove blood components and to reduce formation of magnetic particle aggregates. In order to effectively wash bound targets, the magnet was removed and captured magnetic material was resuspended in wash buffer, followed by reapplication of the magnetic field and capture of the magnetic material in the same flow-through capture cell.

Removal of the captured labeled targets was possible after moving magnets away from the capture chamber and eluting with flow of buffer solution.

What is claimed is:

1. A method for analyzing a bacterium from a sample, the method comprising:
   providing a vessel that contains a body fluid sample comprising a bacterium;
   introducing to the sample in the vessel, magnetic particles comprising a bacterium-specific binding moiety and a buffer that promotes binding of the particles to the bacterium in order to create a mixture containing bacterium/magnetic particle complexes;

flowing the mixture from the vessel into a fluidic device through a channel in the fluidic device and toward a magnet;

applying a magnetic field to isolate the bacterium/magnetic particle complexes from the sample; and analyzing the bacterium.

2. The method according to claim 1, further comprising washing with a wash solution that reduces particle aggregation.

3. The method according to claim 1, wherein the particles are superparamagnetic particles.

4. The method according to claim 3, wherein the particles have a diameter from about 100 nm to about 250 nm.

5. The method according to claim 4, wherein the particles are at least about 65% magnetic material by weight.

6. The method according to claim 1, wherein the bacterium-specific binding moiety is an antibody.

7. The method according to claim 6, wherein the antibody comprises a detectable label.

8. The method according to claim 1, wherein the body fluid is blood.

9. The method according to claim 8, wherein the bacterium is a blood borne bacterium.

10. The method according to claim 1, wherein identifying step comprises sequencing nucleic acid derived from the bacterium or amplifying nucleic acid derived from the bacterium.

11. The method of claim 1, wherein said buffer comprises sodium chloride.

12. The method of claim 11, wherein said buffer further comprises tri(hydroxymethyl)aminomethane-hydrochloric acid (Tris-HCl) and polysorbate 20.

13. The method of claim 12, wherein said Tris-HCl is concentration of about 75 mM.

14. The method of claim 1, wherein said buffer is present in said mixture at a ratio of about 1:1 with said sample.

15. The method of claim 1, wherein the fluidic device is a microfluidic device.

16. The method of claim 1, further comprising incubating the mixture in the vessel to allow the magnetic particles to bind to the bacterium and form bacterium/magnetic particle complexes.

17. A method for detecting a bacterium from a sample, the method comprising:

providing a vessel that contains a body fluid sample comprising a bacterium;

introducing to the sample in the vessel, magnetic particles comprising a bacterium-specific binding moiety and a buffer that promotes binding of the particles to the bacterium in order to create a mixture;

incubating the mixture in the vessel to allow the particles to bind to the bacterium in the sample and form bacterium/magnetic particle complexes;

flowing the mixture from the vessel into a fluidic device through a channel and toward a magnet;

applying a magnetic field to isolate bacterium/magnetic particle complexes from the sample; and detecting the bacterium.

* * * * *